United States Patent [19]

Lippman et al.

[11] Patent Number: 5,462,688
[45] Date of Patent: Oct. 31, 1995

[54] FLOWABLE, PUMPABLE CLEANING COMPOSITIONS AND METHOD FOR THE PREPARATION THEREOF

[75] Inventors: Jerome Lippman; Michael J. Dolan; John J. Sullivan, Jr.; John H. Viscovitz, all of Akron, Ohio

[73] Assignee: GOJO Industries, Inc., Guyahoga Falls, Ohio

[21] Appl. No.: 109,427

[22] Filed: Aug. 20, 1993

[51] Int. Cl.⁶ ........................................ C11D 9/22
[52] U.S. Cl. .......................... 252/89.1; 252/108
[58] Field of Search ..................... 252/108, 89.1

[56] References Cited

U.S. PATENT DOCUMENTS

| | | | |
|---|---|---|---|
| 4,514,318 | 4/1985 | Rodriguez | 252/315.3 |
| 4,617,148 | 10/1986 | Shields | 252/547 |
| 4,621,749 | 11/1986 | Kanfer | 222/153 |
| 4,715,517 | 12/1987 | Potter et al. | 222/181 |
| 4,851,394 | 7/1989 | Kubodera | 514/54 |
| 4,978,036 | 12/1990 | Burd | 222/207 |
| 5,008,108 | 4/1991 | Rha et al. | 424/401 |
| 5,032,311 | 7/1991 | Otsuji et al. | 252/174.17 |
| 5,059,577 | 10/1991 | Hatton | 502/404 |
| 5,204,103 | 4/1993 | Westerhof et al. | 424/195 |

*Primary Examiner*—José G. Dees
*Assistant Examiner*—Joseph M. Conrad, III
*Attorney, Agent, or Firm*—Reese Taylor

[57] ABSTRACT

An originally viscous, non-flowable and non-pumpable cleaning composition made less viscous, flowable and pumpable by the addition of psyllium husks to the composition. The cleaning composition includes an oil phase including at least one of a hydrocarbon oil and a hydrocarbon solvent and mixtures thereof, and at least one of a fatty acid and a non-fatty acid soap surfactant; and the water phase including water and a base. The addition of psyllium husks in various amounts relative to the amount of water in the composition makes the composition flowable. In particular, the addition of from about 2 to about 38 percent by weight of psyllium husks has been found to be suitable to provide a flowable composition containing between about 30 and 55 percent water. A method for the preparation of flowable cleaning compositions is also provided. The cleaning composition (13) forms a novel combination with a container (10) as a replacement element for dispensing apparatus.

28 Claims, 1 Drawing Sheet

FLOWABLE, PUMPABLE CLEANING COMPOSITIONS AND METHOD FOR THE PREPARATION THEREOF

TECHNICAL FIELD

The present invention relates to emulsion gel cleaning compositions. More particularly, the present invention relates to emulsion gel cleaning compositions which are less viscous than previous emulsion gel cleaning compositions, thereby making them flowable and/or pumpable. Specifically, the present invention relates to the addition of psyllium husks to a viscous non-flowable, non-pumpable, cleaning composition to provide a less viscous, flowable and pumpable cleaning composition.

BACKGROUND OF THE INVENTION

Emulsion gel cleaning compositions are well known in the art. For example, one well known emulsion gel cleaning composition is commercially available from the Assignee of record under the registered trademark GOJO. Such compositions are also referred to as "waterless"; however, it should be understood, that the term "waterless" refers to the fact that the cleaning composition does not require the use of water together with the cleaning composition in order to clean dirt and grease from the skin. It does not mean that the cleaning composition does not include water. In fact, most, if not all, "waterless" emulsion gel cleaning compositions do indeed contain water in the composition.

Among the most significant problems associated with emulsion gel cleaning compositions is the fact that many formulations of the compositions are viscous, and therefore, are not flowable or pumpable. Thus, they are unsuitable for use in many dispensers as for example, so called bag-in-box dispensing apparatus of the type disclosed in U.S. Pat. Nos. 4,621,749 and 4,715,517 owned by the assignee of record, and rigid wall refill apparatus of the type disclosed in U.S. Pat. No. 4,978,036, the subject matters of which are incorporated herein by reference. Emulsion gel cleaning compositions are also generally unsuited for conventional squeeze bottles, requiring instead open top containers which can be dipped into by hand.

Heretofore, in order to make the cleaning compositions flowable and/or pumpable, the amount of water employed in the composition formulations was required to be either increased significantly or decreased significantly. For example, at least one known emulsion gel cleaning composition requires formulations wherein water comprises less than about 26 percent by weight or more than about 52 percent by weight of the total composition in order to be flowable and/or pumpable. However, such formulations are not considered to be optimal for this cleaning composition inasmuch as the cleaning performance and physical stability are severely reduced.

Thus, a cleaning composition which is less viscous than conventional emulsion gel cleaning compositions and which is flowable and/or pumpable for formulations of the composition containing optimal amounts of water is desirable.

SUMMARY OF INVENTION

It is therefore an object of the present invention to provide a cleaning composition which is less viscous than prior compositions employing the same amounts of water.

It is another object of the present invention to provide a cleaning composition, as above, which is flowable and/or pumpable.

It is yet another object of the present invention to provide a cleaning composition, as above, that is suitable as a skin soap and may be dispensed from a pump dispenser.

It is yet another object of the present invention to provide a cleaning composition, as above, that is suitable as a skin soap and may be dispensed from a bag-in-box dispenser.

It is still another object to provide a method for making a flowable, emulsion gel cleaning composition.

At least one or more of the foregoing objects of the present invention, as well as the advantages thereof over the known art relating to emulsion gel cleaning compositions, which shall become apparent from the description which follows, are accomplished by the invention as hereinafter described and claimed.

In general, it has been found that these and other objects can be achieved by adding psyllium husks to an originally non-flowable cleaning composition. That is, the present invention provides a cleaning composition comprising an oil phase including at least one of a hydrocarbon oil and a hydrocarbon solvent and mixtures thereof, and at least one of a fatty acid and a non-fatty acid soap surfactant; a water phase containing water and a base; and an effective amount of psyllium husks to make the composition flowable.

The present invention also provides a flowable cleaning composition containing psyllium husks. The present invention further provides in combination, a container and an emulsion gel cleaning composition contained therein, the container being sealed and providing at least one port for the release of the emulsion gel cleaning composition, the composition comprising an oil phase including at least one of a hydrocarbon oil and a hydrocarbon solvent and mixtures thereof, and at least one of a fatty acid and a non-fatty acid soap surfactant; a water phase containing water and a base; and an effective amount of psyllium husks to make the composition flowable.

The present invention also includes a method for making an originally non-flowable cleaning composition flowable comprising the step of adding psyllium husks to at least a portion of the composition.

BRIEF DESCRIPTION OF THE DRAWINGS

The drawing FIGURE is a perspective view of a bag containing a flowable emulsion gel cleaning composition housed in a box, a portion of which has been broken away.

PREFERRED EMBODIMENT FOR CARRYING OUT THE INVENTION

Figure 1:
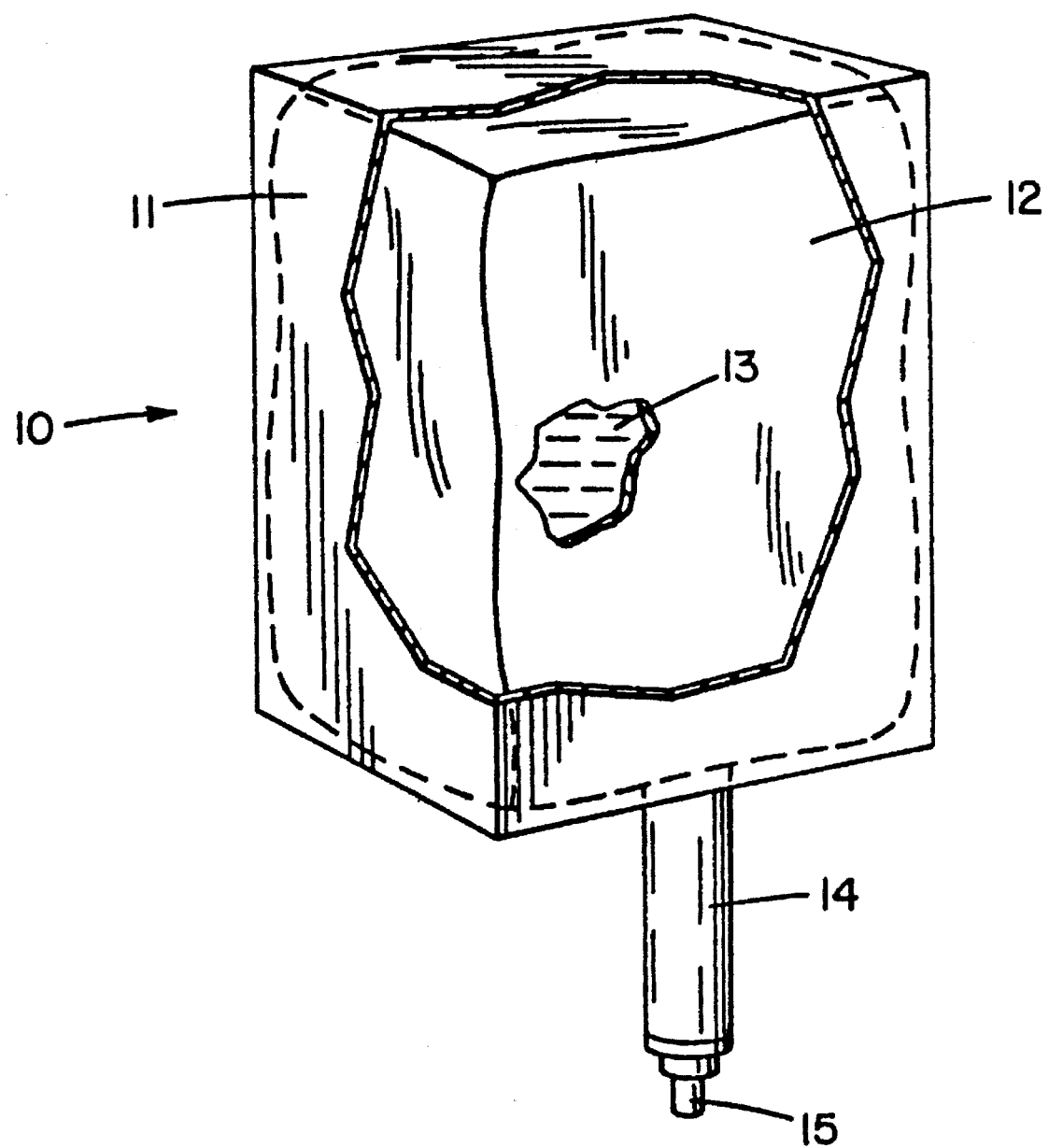

A unique property of the emulsion gel cleaning compositions of the present invention is pumpability, which aids dispensing. With reference to the drawing figure, a practical use for this property is illustrated. The drawing figure presents a package or container, generally 10, with portions broken away to present the interior. The container includes a relatively rigid outer box 11 and a flexible inner bag 12. The emulsion gel cleaning composition 13 is carried in the bag 12 which, due to its flexible nature, collapses as the composition is withdrawn. The container typically provides a tube 14, communicating directly with the bag 12, through which the gel is conducted for dispensing. A one-way valve or other suitable port 15 is typically provided to provide the gel into the hand of the user or other desired receptacle.

As noted hereinabove, such containers include disposable refill cartridges which can be readily loaded into and removed from known dispensing apparatus (not shown).

Heretofore, such devices have enjoyed success with liquid and cleaning compositions because the latter readily flow via gravity out of the bag 12. As a significant improvement over prior art compositions, the present invention provides an emulsion gel composition, having a viscosity making it flowable and pumpable through such containers. Of course, it is to be appreciated that the present invention is not necessarily limited to usage in a particular type of container, cartridge refill or dispensing apparatus, the container 10 having been depicted merely for purposes of exemplification. Thus, as used herein, the term container is used in the broadest sense to include receptacles for the gel, cartridge refills, squeeze bottles and the like.

As noted hereinabove, the invention herein is directed toward a cleaning composition, typically in the form of an emulsion or an emulsion gel, which is made flowable by the addition of psyllium husks. The composition of the present invention preferably includes an oil phase and a water phase, the oil phase containing at least one of a hydrocarbon oil and a hydrocarbon solvent, and at least one of a fatty acid and a surfactant, and the water phase containing water and some sort of alkali or amine base. However, it will be understood that each ingredient is not necessarily required to be added as a part of a phase, that is, the ingredients can be added independently of one another regardless of the phase. Nevertheless, for ease of discussion, the different components are discussed with regard to the oil and water phases.

Numerous other components such as fragrances, dyes, colorants, pigments, preservatives, emollients, thickeners, abrasives and the like can also be utilized. Such cleaning compositions are suitable for use as a soap, and especially suitable as a hand soap in that they remove both dirt and grease and do not require water. However, without the addition of the psyllium husks, many formulations of the cleaning composition are not flowable and/or pumpable. Accordingly, the psyllium husks are added to reduce the viscosity of the composition, thereby making the cleaning composition flowable and pumpable and allowing the composition to be used in pump dispensers and the like.

With respect to the oil phase of the composition, the hydrocarbon oils and solvents are well known in the art. The hydrocarbon oil component is an oil which generally cuts and dissolves viscous organic materials such as grease, sludge and the like. Generally, any non-drying and non-irritating organic mineral oil can be utilized. More specifically, petroleum mineral oils such as the aliphatic and wax-based oils can be utilized, the aromatic or asphalt-based oils can be utilized, or the mixed-based oils can be utilized. One desirable oil is white mineral oil which is obtained by refining any of the three basic types of crude oil. White mineral oils were initially known as Russian oils. There are generally two types of white mineral oil. One type, which has a kinematic viscosity of not more than 37 centipoise at 100° F., is termed "light" whereas the other type of oil, having a kinematic viscosity of not less than 38.1 centipoise at 100° F., is termed "heavy". For the present invention, either type is suitable for use therein. Mineral oils are readily available from a large number of manufacturers as set forth on page 172 of the CTFA Dictionary, 3rd Ed., The Cosmetic, Toiletry and Fragrance Association, Inc., of Washington, D.C., (1982) which is hereby incorporated by reference with regard to the types and manufacturers of mineral oil.

Another mineral type oil which can be utilized in the present invention is mineral seal oil. Additionally, another example of a hydrocarbon oil is the various isoparaffinic oils. Other hydrocarbon oils are well known in the art and in the literature. Accordingly, conventional hydrocarbon oils can be utilized in addition to those set forth herein.

Notably, all or a portion of the hydrocarbon oil can be extended with conventional or common solvents complementary to or compatible with the hydrocarbon oils. Such solvents include, for example, odorless or low odor hydrocarbon solvents, stoddard solvents, limonene, dipentene and the like. One such suitable solvent commonly used is odorless mineral spirits. In regard to the present invention, petroleum distillate materials such as those designated by CAS Nos. 8012-95-1, 8032-32-4, 8042-47- 5, 8042-41-3, 64741-44-2, 64742-14-9, 64742-46- 7, 64742-47-8, 64742-48-9, 64742-55- 8, 64742-65-7, 64742-88-7, and 64771-72-8 as well as plant-derived solvents, such as d-limonene, dipentene and the like can be employed.

Generally, the hydrocarbon oil and solvent comprise from about 25 to about 60 percent by weight of the total composition which can, in turn, comprise all mixtures of oil and solvent from 0 to 100 parts by weight of each to total 100 parts of hydrocarbon oil/solvent. Desirably, the oil and solvent includes from about 30 to about 55 percent by weight and preferably from about 40 to about 55 percent by weight of the total composition.

The fatty acid in the oil phase of the composition may include a variety of oils and fats having from about 6 to about 20 carbon atoms. Typical, useful fatty acids and their respective number of carbon atoms include the following:

| Caproic acid | 6 |
| --- | --- |
| Caprylic acid | 8 |
| Capric acid | 10 |
| Lauric acid | 12 |
| Myristic acid | 14 |
| Myristoleic acid | 14 |
| Palmitic acid | 16 |
| Palmitoleic acid | 16 |
| Oleic acid | 18 |
| Linoleic acid | 18 |
| Linolenic acid | 18 |
| Stearic acid | 18 |

Typical commercial blends such as oleic fatty acid, coconut fatty acid, soya fatty acid and tall oil fatty acid can be utilized. Preferably, the fatty acid comprises from about 5 to about 10 percent by weight of the total composition.

As is well known, the fatty acid or a fatty acid ester is commonly used in conjunction with an alkali or base from the water phase to form a soap. By the term "soap", it is meant a conventional soap, that is, the salt of a fatty acid. More specifically, they are the water-soluble reaction product of a fatty acid or a fatty acid ester with an alkali or the reaction product of a fatty acid or fatty acid ester with a base such as an amine. Where a base is utilized, organic alkalis or amines such as monoethanolamine, diethanolamine, triethanolamine and mixed isopropanolamines such as diisopropanolamine are frequently used to neutralize the fatty acid and generally produce a soap which has good water solubility as well as oil solubility properties and hence, is an excellent emulsifier. Inorganic alkalis such as potassium hydroxide, sodium hydroxide, ammonium hydroxide, soda ash and ammonia may also be used.

In addition, one or more non-fatty acid soap surfactants can be included in the oil phase of the cleaning composition in amounts preferably ranging from about 2 to about 10 percent by weight. A surfactant is generally any substance which reduces the surface tension of a liquid. Nonionic surfactants, i.e., surfactants which are uncharged (neutral) and without cationic or anionic sites, are preferred since they tend to render the composition meta stable, i.e., impart two desirable properties thereto. The first property is that of a suitable long shelf life. In other words, the emulsion can be held together at room temperature for long periods of time. The second desirable property is that upon use of the cleaning composition, the surfactant permits breakage of the emulsion or opening up thereof such that the hydrocarbon oil is readily released.

Numerous surfactants can be utilized and are well known in the art. In conjunction therewith, reference is made to McCutcheon, *Detergents and Emulsifiers*, 1992 Noah American Edition, Glen Rock, N.J. which is hereby incorporated by reference with regard to the desired surfactants, whether nonionic, anionic, cationic or amphoteric. In addition, another reference listing the various surfactants is the *CTFA Cosmetic Ingredient Dictionary*, 3rd Edition, published by the Cosmetic, Toiletry and Fragrance Association, Inc., Washington, D.C., (1982) which is also hereby incorporated by reference with regard to surfactants and especially nonionic surfactants. Example of nonionic surfactants suitable for use in the oil phase of the cleaning composition include linear alcohol ethoxylates, branched alcohol ethoxylates, and alkyl phenol ethoxylates, with a linear alcohol ethoxylate, available and sold commercially by Shell Chemical Co. under the registered trademark Neodol®23-5, being particularly suitable.

Art optional component of the cleaning composition generally found in the oil phase is a solubilizer such as propylene glycol, sorbitol, glycerin, and the like. Solubilizers are utilized to help maintain various additives, set forth hereinbelow, in solution which otherwise are not generally soluble in water, as for example various fragrances, preservatives and the like. They also impart mildness to the cleaning composition and impart good freeze-thaw properties. Examples of other suitable solubilizers are known in the art as well as the literature. The amount of such solubilizers generally ranges from about 1 to about 5 percent by weight and desirably from about 1 to about 3 percent by weight.

In order to form an emulsion, water is used and is the most common and abundant ingredient in the water phase. The amount of water can vary extensively based upon the type of cleaning composition desired, e.g., an emulsion, an emulsion gel, etc. Typically, the amount utilized is from about 30 to about 55 percent by weight, with about 30 to about 46 percent by weight being preferred. Significantly, however, many formulations of the cleaning composition are not flowable and/or pumpable when water is utilized at certain percentages. For example, as discussed herein, at least one cleaning formulation is not flowable where from about 26 to about 52 percent by weight water is used in the composition.

In addition, as previously discussed with respect to the fatty acid employed in the present inventive composition, the water phase may also include a base such as an amine or a hydroxide. Where such a base is employed, it is preferred that from about 0.2 to about 5 percent by weight be employed. The base is utilized in conjunction with the fatty acid to produce a soap on an equivalent basis of from about 2.7 to 0.8 equivalents to 1 equivalent of base. Examples of suitable base include organic alkalis or amines such as monoethanolamine, triethanolamine, and mixed isopropanolamines such as diisopropanolamine. Examples of suitable base also include inorganic alkalis, such as potassium hydroxide, sodium hydroxide, ammonium hydroxide and ammonia.

In order to make the cleaning composition flowable, psyllium husks are added to the composition. Psyllium husks are the cleaned, dried seed coat or epidermis, separated by conventional methods such as winnowing and thrashing, from the seeds of *Plantago ovata forskal*, known in commerce as Blond Psyllium, Indian Psyllium or Ispaghula, or from *Plantago psyllium linne* or from *Plantago indica linne*, or from *Plantago arenaria waldstein et kitaibel*, known in commerce as Spanish or French Psyllium (Fam. Plantaginacae). The psyllium husk or seed coat (epidermis) is composed of large cells with transparent walls filled with mucilage. This mucilage comprises about 98% of the psyllium seed husk and is a natural polysaccharide. As such, it may include xylose, arabinose, rhamnose, galactose, galacturonic acid, 4-0-methyl glucuronic acid and 2-0-(2-D-galactopyranosyluronic acid)-L-rhamnose. Notably, the primary active characteristic of psyllium husks is their ability to absorb many times their own weight of water. This ability to absorb water, also known as the swell volume of the product is detailed in a U.S. Pharmacopeia XXI procedure set forth in the Official Monograph for Plantago Seed.

There are three methods preferably by which to add the psyllium to the composition. First, the psyllium can be added with stirring after the water and oil phases have already been stirred into a smooth homogeneous gel. The base formulation is typically produced in this manner. Second, the ingredients can be added individually with stirring in the order noted hereinbelow in Table I with the psyllium being added between water and monoethanolamine. Third, the psyllium could be added to the oil phase with stirring prior to the addition of the water phase. Accordingly, any of these methods of addition can be employed for the addition of psyllium to the cleaning formulations.

Finally, various other common and conventional additives can be utilized in suitable or conventional amounts. Examples of such additives include preservatives, colorants, dyes, pigments, fragrances, emollients, thickeners, abrasives and the like, the total amount of such additives is generally small and typically within the range of from about 0.5 to about 3 percent by weight when present, with from about 1 to about 2 percent by weight being preferred for additives other than abrasives. For the abrasives, from about 1 to about 10 percent by weight can be employed when desired, with from about 4 to about 6 percent by weight being preferred. Additives with the exception of abrasives can be added to the waterphase, oil phase or stirred into the homogenous gel depending on solubility and material compatibility. It is preferred that most abrasives be added last with stirring.

The use of thickening agents in detergent and cosmetic compositions is well known. Various materials similar to, and including psyllium husks have been shown to increase viscosity and reduce flowability of these types of compositions.

The addition of particulate solids, as for example abrasives such as pumice, will also increase the viscosity and reduce flowability of waterless emulsion cleaning compositions. Surprisingly, it has been found that the addition of psyllium husks to such compositions renders them not more viscous but rather less viscous and in fact flowable and pumpable. Even more surprisingly, the addition of psyllium husks can reverse the thickening effects of abrasives and render even abrasive-containing compositions flowable and pumpable.

The abrasive particles can be of the same type of abrasive or of different types. The abrasives are generally finally divided particles and, depending on the desired end use, they can be hard or mild.

Examples of hard abrasives generally include silica sand, aluminum oxide (corundum), pumice, rouge (iron oxide), feldspar, silicon carbide, boron carbide, cerium oxide, quartz, garnet, and the like. Hard abrasives can loosely be defined as those compounds, either natural, mineral or synthetic which have a hardness on the Mohs scale of from about 6 to 10.

Other suitable abrasives, generally classified as mild abrasives (Mohs value of about 6 or less), include compounds such as titanium dioxide, calcium carbonate, calcium phosphate, diatomaceous earth, various forms of borax including puffed borax, perlite, kaolinite, mica, tripoli, pumicite and expanded pumicite, various ground rigid polymeric or synthetic plastics materials such as polyethylene, melamine, urea formaldehyde resins, or polyurethane foam, talc, vermiculite, water absorbent soft abrasives such as calcium silicate, aluminum silicate, and the like, wood flour, coconut shell, walnut flour, walnut shell, corn cob and the like. Basically, substantially any material that can be ground into particles could be employed.

Desirable abrasives for use in the present invention include limestone (calcium carbonate), pumice, and various ground plastics. Pumice is a preferred hard abrasive and perlite is a preferred mild abrasive. Perlite is a preferred material because it is crushable. Crushable abrasives are those which break up or disintegrate into smaller particles under the application of mild pressure, such as hand pressure exerted during washing. Perlite, a generic term for naturally occurring silicaceous volcanic rock, is generally chemically inert and has a pH of approximately 7.

A broad range of particle sizes can usually be employed, however, particles which generally pass through a U.S. standard No. 40 mesh screen are usually selected for desired handfeel.

In order to demonstrate practice of the invention, a typical viscous emulsion gel cleaning composition was prepared. The exact amounts of each ingredient utilized is disclosed in Table I. This conventional emulsion gel cleaning composition is well known in the art and has been utilized by the Assignee of record as such. However, due to the viscosity of the composition, it is not useful in many pump dispensers and the like.

TABLE I

CONVENTIONAL WATERLESS CLEANING COMPOSITION

| | INGREDIENTS | PERCENT BY WEIGHT |
|---|---|---|
| Oil phase | Odorless Mineral Spirits | 37.67 |
| | Technical Mute Mineral Oil | 10.02 |
| | Oleic acid | 7.07 |
| | Linear alcohol Ethoxylate$_a$ | 4.32 |
| | Propylene Glycol | 2.00 |
| Water Phase | Water | 37.75 |
| | Monoethanolamine | 1.17 |
| Additives | Perfume, color, preservative, etc. | As desired | a) Nonionic surfactant, Neodol ® 23-5, available from Shell Chemical Co.

Typically, as noted hereinabove, the conventional cleaning composition can be prepared by pouring the water phase into the oil phase with stirring until a homogeneous smooth gel is formed. It is possible, however, to add each ingredient individually. Generally, when this is done, it is preferred that the ingredients be added in the order set forth hereinabove in Table I.

For the present invention, the amount of water added to the composition was varied. The amounts of water utilized varied between 25.74 percent by weight and 51.76 percent by weight. Amounts of water in between this range included 29.7 percent, 33.75 percent, 37.75 percent, 41.76 percent and 45.76 percent. These formulations became the control or base compositions for determining viscosity and other data as detailed hereinbelow.

At this point, it should be understood that, because the amount of water was varied and, in instances other than for the base compositions, psyllium was added, the percentage by weight of the other ingredients of the composition likewise varied to properly correlate with each other. Accordingly, it will be understood that all ingredients of the composition add to total 100 percent. For example, Table II presents the Base Formula with 29.74 percent by weight water and the same formula (Final Formula) utilizing the 29.74 percent formula with the addition of 6.00 percent by weight psyllium. As can be seen the percent by weight of each of the ingredients in the Final Formula has correspondingly decreased.

TABLE II

FORMULA SHOWING THE ADDITION OF PSYLLIUM

| Ingredient | Base Formula | Final Formula |
|---|---|---|
| Odorless Mineral Spirits | 42.51 | 39.96 |
| Technical White Mineral Oil | 11.31 | 10.63 |
| Oleic Acid | 7.99 | 7.51 |
| Linear alcohol Ethoxylate | 4.87 | 4.58 |
| Propylene Glycol | 2.26 | 2.12 |
| Water | 29.74 | 27.96 |
| Monoethanolamine | 1.32 | 1.24 |
| Psyllium | — | 6.00 |
| Total | 100.00 | 100.00 |

The actual mixing procedure employed for the Final Formula composition was prepared by the following procedure:

1. To a 4 quart Hobart/Kitchenaid mixing bowl was added:

Odorless Mineral Spirits 959.04 grams

Technical White Mineral Oil 255.12 grams

Oleic Acid 180.24 grams

Neodol®23-5 109.92 grams

Propylene Glycol 50.88 grams

2. Place mixing bowl on Hobart/Kitchenaid Mixer (model K45SS or equivalent). Begin mixing at speed 2.

3. To a 1000 ml beaker was added: Soft water 671.04 grams Monoethanolamine 29.76 grams 4. Mix ingredients in 1000 ml beaker thoroughly with a glass stirring rod.

5. Slowly add ingredients in 1000 ml beaker to the mixing bowl with mixing at speed 2.

6. Continue mixing until an homogenous smooth gel is formed.

7. When homogenous smooth gel is formed slowly add 144 grams of psyllium material to the mixing bowl.

8. Continue mixing at speed 2 until a smooth lotion with no lumps is observed.

The base compositions were tested for viscosity, flowability and pumpability. For viscosity, measurements were made using a Brookfield Model RVTD viscometer with spindle T-D at speeds 10, 1 and 0.5. For the flowability and pumpability determinations, strokes to prime and output data were obtained utilizing a Calmar System 8 Dispenser. Accordingly, the flowability/pumpability determination was made relative to pumpability. A strokes-to-prime result of less than 50 strokes and any consistent output result was determined to be flowable/pumpable. All of the test samples were prepared and remained at ambient room temperature (approximately 74° F., 23.3° C.), and all measurements were made approximately 24 hours after completion of the batch formulation.

More specifically, viscosity was measured as follows:

1. Place sample 24 hours after batch completion at ambient temperature in a suitable container.
2. Utilizing Brookfield Model RVTD viscometer with heliopath stand and T-D spindle obtain sample viscosity at speed 10, 1 or 0.5 depending on scale reading.

Strokes to prime and output were determined as follows:

1. Place sample 24 hours after batch completion into suitable container.
2. Insert Calmar pump (System 8 dispenser D8N Calmer Drawing No. CS 1222) into sample.
3. Determine the number of strokes on the pump it takes to produce flow or output. Record as Strokes to Prime.
4. Continue to pump until stable/consistent flow is obtained.
5. Obtain weight of 10 consecutive strokes of pump. Record as Output.

Based upon the data obtained with respect to the base formulations, it was found that formulations at 25.74 percent by weight water and at 51.76 percent by weight water were flowable and pumpable without the use of psyllium husks. Accordingly, various amounts of psyllium husks were added to the viscous base formulations containing different amounts of water ranging between 29.74 percent weight and 45.76 percent by weight to determine the amount of psyllium husks required to convert viscous non-flowable, non-pumpable formulations into less viscous flowable and/or pumpable formulations. For each formulation, viscosity, strokes to prime and output in grams were measured using the same instruments and methods described hereinabove for the base formulations. The data obtained from these tests are disclosed in Tables III to V hereinbelow.

TABLE III

| | VISCOSITY (in centipoise) | | | | | | |
|---|---|---|---|---|---|---|---|
| | 25.74% WATER | 29.74% WATER | 33.75% WATER | 37.75% WATER | 41.76% WATER | 45.76% WATER | 51.76% WATER |
| BASE | 59,600 | 127,200 | 1,272,000 | 1,234,000 | 904,000 | 108,400 | 2,000 |
| 2% PSYLLIUM | | 44,800 | 86,200 | 1,434,000 | | 150,400 | |
| 4% PSYLLIUM | | | | 102,400 | | | |
| 6% PSYLLIUM | | 12,000 | 4,800 | 4,000 | 68,400 | 96,000 | |
| 8% PSYLLIUM | | | | 16,800 | | | |
| 10% PSYLLIUM | | 8,600 | 11,000 | 18,400 | 12,600 | 13,200 | |
| 12% PSYLLIUM | | 7,000 | | | 23,000 | | |
| 14% PSYLLIUM | | 7,000 | 7,400 | | | 25,400 | |
| 16% PSYLLIUM | | | | | 16,000 | | |
| 18% PSYLLIUM | | 8,200 | 11,200 | | | 18,600 | |
| 28% PSYLLIUM | | 34,600 | 96,400 | | | 179,400 | |
| 38% PSYLLIUM | | 66,800 | 314,000 | | | 1,270,000 | |
| 48% PSYLLIUM | | >4,000,000 | >4,000,000 | | | >4,000,000 | |

TABLE IV

| | STROKES TO PRIME | | | | | | |
|---|---|---|---|---|---|---|---|
| | 25.74% WATER | 29.74% WATER | 33.75% WATER | 37.75% WATER | 41.76% WATER | 45.76% WATER | 51.76% WATER |
| BASE | 15 | >200 | >200 | >200 | >200 | >200 | 6 |
| 2% PSYLLIUM | | 11 | >200 | >200 | | >200 | |
| 4% PSYLLIUM | | | | 17 | | | |
| 6% PSYLLIUM | | 6 | 5 | 6 | 12 | 27 | |
| 8% PSYLLIUM | | | | 8 | | | |
| 10% PSYLLIUM | | 6 | 6 | 7 | 7 | 9 | |
| 12% PSYLLIUM | | 5 | | | 9 | | |
| 14% PSYLLIUM | | 5 | 6 | | | 6 | |
| 16% PSYLLIUM | | | | | 8 | | |
| 18% PSYLLIUM | | 5 | 6 | | | 7 | |
| 28% PSYLLIUM | | 5 | 28 | | | >200 | |
| 38% PSYLLIUM | | 7 | 41 | | | >200 | |
| 48% PSYLLIUM | | >200 | >200 | | | >200 | |

TABLE V

| | OUTPUT (in grams, per 10 strokes, after priming) | | | | | | |
|---|---|---|---|---|---|---|---|
| | 25.74% WATER | 29.74% WATER | 33.75% WATER | 37.75% WATER | 41.76% WATER | 45.76% WATER | 51.76% WATER |
| BASE | 19.45 | 0.00 | 0.00 | 0.00 | 0.00 | 0.00 | 32.40 |
| 2% PSYLLIUM | | 12.31 | 0.00 | 0.00 | | 0.00 | |
| 4% PSYLLIUM | | | | 15.02 | | | |
| 6% PSYLLIUM | | 26.64 | 26.81 | 30.72 | 14.6 | 8.60 | |
| 8% PSYLLIUM | | | | 28.74 | | | |
| 10% PSYLLIUM | | 31.14 | 29.04 | 29.64 | 28.63 | 25.58 | |
| 12% PSYLLIUM | | 31.74 | | | 28.46 | | |
| 14% PSYLLIUM | | 30.10 | 30.81 | | | 30.90 | |
| 16% PSYLLIUM | | | | | 27.55 | | |
| 18% PSYLLIUM | | 29.46 | 28.98 | | | 31.24 | |
| 28% PSYLLIUM | | 27.80 | 17.55 | | | 0.00 | |
| 38% PSYLLIUM | | 17.04 | 4.03 | | | 0.00 | |
| 48% PSYLLIUM | | 0.00 | 0.00 | | | 0.00 | |

As can be clearly seen from the pumpability data in Tables IV to V, the addition of from about 2 to about 38 percent by weight psyllium husks to the viscous non-flowable, non-pumpable base formulations yielded a flowable and pumpable composition for at least some of the formulations. Generally, these were the formulations having a lower water percentage. However, the addition of from about 6 to about 18 percent by weight of psyllium husks yielded flowable and pumpable compositions for all formulations tested.

While not wishing to be bound with respect to the viscosity measurements, it was found that formulations having a viscosity greater than about 904,000 cps were non-flowable, while formulations having a viscosity below about 68,400 cps were flowable without exception. Those formulations having viscosities between 86,200 cps and about 314,000 cps were non-flowable about one-half the time. It is to be appreciated that these viscosity ranges will vary with the particular dispensing equipment with which the composition is to be employed. Moreover, it has also been found that as the water content increased, greater amounts of psyllium were required to initiate the effect. Additionally, it has been found that the higher the water content, the more narrow the range of psyllium husk addition that will produce a flowable, pumpable formulation.

It is also to be appreciated that the compositions of the present invention can be utilized in bag-in-box dispensers, thereby lending the utility of such apparatus to use with emulsion gel cleaning compositions. Maximum viscosity ranges that can be utilized with bag-in-box dispensers is approximately 24,000 to 40,000 cps. This viscosity limit for bag-in-box dispensers is primarily due to the fact that the flexible bag cannot be completely emptied of its contents if the product has high viscosity.

Thus it should be evident that the composition and method of the present invention are highly effective in providing a flowable cleaning composition. The invention is particularly suited for skin or hand soaps, but is not necessarily limited thereto. The composition of the present invention can be used separately with equipment other than pump dispensers and the like such as squeeze bottles.

Based upon the foregoing disclosure, it should now be apparent that the use of the flowable cleaning composition described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, the various oil phase components and water phase components are not necessarily limited to those disclosed in the examples herein, it being understood that other similar components may be utilized. Thus, the scope of the invention shall include all modifications and variations that may fall within the scope of the attached claims.

What is claimed is:

1. A cleaning composition comprising:
   an oil phase including at least one of a hydrocarbon oil and a hydrocarbon solvent and mixtures thereof, and at least one of a fatty acid and a non-fatty acid soap surfactant;
   a water phase containing water and a base; and
   an effective amount of psyllium husks to make the composition flowable.

2. A cleaning composition according to claim 1, wherein the amount of said hydrocarbon oil is from 0 to 100 parts by weight and said hydrocarbon solvent is from 0 to 100 parts by weight to total 100 parts by weight and comprise from about 25 to about 60 percent by weight of said cleaning composition.

3. A cleaning composition according to claim 2, wherein said hydrocarbon oil is white mineral oil and said hydrocarbon solvent is odorless mineral spirits.

4. A cleaning composition according to claim 1, wherein the amount of said water is from about 30 to about 55 percent by weight and wherein the amount of said psyllium husks is from about 2 to about 38 percent by weight.

5. A flowable cleaning composition according to claim 4, wherein said composition has a viscosity of less than 314,000 cps.

6. A flowable cleaning composition according to claim 5, wherein said composition has a viscosity of less than 68,400 cps.

7. A cleaning composition according to claim 1, wherein the amount of said water is from about 30 to about 46 percent by weight and wherein the amount of said psyllium husks is from about 6 to about 18 percent by weight.

8. A cleaning composition according to claim 1, wherein the amount of fatty acid is from about 2.7 to about 0.8 equivalents to 1 equivalent of base.

9. A cleaning composition according to claim 8, wherein the reaction product of said fatty acid with said base provides a soap.

10. A cleaning composition according to claim 9, wherein said base is an amine.

11. A cleaning composition according to claim 10, wherein said amine is selected from the group consisting of monoethanolamine and triethanolamine.

12. A cleaning composition according to claim 1, wherein said non-fatty acid soap surfactant is nonionic and the amount of said surfactant is from about 2 to about 10 percent by weight.

13. A cleaning composition according to claim 1, further comprising from about 0.5 to about 3 percent by weight of an additive selected from the group consisting of preservatives, colorants, dyes, pigments, fragrances, emollients and thickeners.

14. A cleaning composition according to claim 1, further comprising from about 1 to about 10 percent by weight of an abrasive.

15. A cleaning composition according to claim 14, wherein said abrasive is selected from the group consisting of perlite, pumice and mixtures thereof.

16. In combination, a container and an emulsion gel cleaning composition contained therein, the container providing at least one port for the release of the emulsion gel cleaning composition, the composition comprising:
   an oil phase including at least one of a hydrocarbon oil and a hydrocarbon solvent and mixtures thereof, and at least one of a fatty acid and a non-fatty acid soap surfactant;
   a water phase containing water and a base; and
   an effective amount of psyllium husks to make the composition flowable.

17. The combination according to claim 16, wherein the amount of said hydrocarbon oil is from 0 to 100 parts by weight and said solvent is from 0 to 100 parts by weight to total 100 parts by weight and comprise from about 25 to about 60 percent by weight of said cleaning composition.

18. The combination according to claim 16, wherein the amount of said water is from about 20 to about 55 percent by weight and wherein the amount of said psyllium husks is from about 2 to about 38 percent by weight.

19. The combination according to claim 16, wherein the amount of said water is from about 30 to about 46 percent by weight and wherein the amount of said psyllium husks is from about 6 to about 18 percent by weight.

20. The combination according to claim 19, wherein said hydrocarbon oil is white mineral oil and said hydrocarbon solvent is odorless mineral spirits.

21. The combination according to claim 16, wherein the amount of fatty acid is from about 2.7 to about 0.8 equivalents to 1 equivalent of base.

22. The combination according to claim 21, wherein the reaction product of said fatty acid with said base provides a soap.

23. The combination according to claim 22, wherein said base is an amine.

24. The combination according to claim 23, wherein said amine is selected from the group consisting of monoethanolamine and triethanolamine.

25. The combination according to claim 16, wherein said non-fatty acid soap surfactant is nonionic and the amount of said surfactant is from about 2 to about 10 percent by weight.

26. The combination according to claim 16, further comprising from about 0.5 to about 3 percent by weight of an additive selected from the group consisting of preservatives, colorants, dyes, pigments, fragrances, emollients and thickeners.

27. The combination according to claim 16, further comprising from about 1 to about 10 percent by weight of an abrasive.

28. The combination according to claim 27, wherein said abrasive is selected from the group consisting of perlite, pumice and mixtures thereof.

* * * * *